(12) United States Patent
Steve

(10) Patent No.: US 9,895,407 B2
(45) Date of Patent: Feb. 20, 2018

(54) DISINFECTING FORMULATIONS AND USES THEREOF

(75) Inventor: Peter Lawrence Steve, Victoria (AU)

(73) Assignee: Sunny Wipes Pty Ltd, Kings Park (AU)

( * ) Notice: Subject to any disclaimer, the term of this patent is extended or adjusted under 35 U.S.C. 154(b) by 30 days.

(21) Appl. No.: 14/232,642

(22) PCT Filed: Jul. 13, 2012

(86) PCT No.: PCT/AU2012/000841
§ 371 (c)(1),
(2), (4) Date: Mar. 21, 2014

(87) PCT Pub. No.: WO2013/006917
PCT Pub. Date: Jan. 17, 2013

(65) Prior Publication Data
US 2014/0234448 A1    Aug. 21, 2014

(30) Foreign Application Priority Data
Jul. 14, 2011   (AU) ................... 2011902822

(51) Int. Cl.
| | | |
|---|---|---|
| *A61K 36/61* | (2006.01) | |
| *A01N 31/02* | (2006.01) | |
| *A01N 65/28* | (2009.01) | |
| A61K 31/045 | (2006.01) | |
| A61K 47/10 | (2017.01) | |
| A61K 47/18 | (2017.01) | |
| A61K 47/22 | (2006.01) | |
| A61K 47/32 | (2006.01) | |

(52) U.S. Cl.
CPC .............. *A61K 36/61* (2013.01); *A01N 31/02* (2013.01); *A01N 65/28* (2013.01); *A61K 31/045* (2013.01); *A61K 47/10* (2013.01); *A61K 47/18* (2013.01); *A61K 47/22* (2013.01); *A61K 47/32* (2013.01)

(58) Field of Classification Search
None
See application file for complete search history.

(56) References Cited

U.S. PATENT DOCUMENTS

| | | |
|---|---|---|
| 6,217,887 B1 | 4/2001 | Beerse et al. |
| 6,423,329 B1 | 7/2002 | Sine et al. |
| 2003/0087885 A1* | 5/2003 | Masini-Eteve et al. ...... 514/177 |
| 2005/0271595 A1* | 12/2005 | Brown ................ A61K 8/0204 424/10.1 |
| 2006/0275218 A1* | 12/2006 | Tamarkin ............... A61K 8/046 424/45 |
| 2008/0181976 A1* | 7/2008 | Fukuda .................... A61K 8/34 424/742 |

FOREIGN PATENT DOCUMENTS

| | | |
|---|---|---|
| CN | 102036691 A | 4/2011 |
| DE | 20 2007 002 978 U1 | 5/2007 |
| EP | 1964576 A1 | 9/2008 |
| WO | WO-2005/084717 A1 | 9/2005 |
| WO | WO 2006/085907 A2 | 8/2006 |
| WO | WO-2009/129585 A1 | 10/2009 |
| WO | WO-2013/006917 A1 | 1/2013 |

OTHER PUBLICATIONS 2015 https://en.wikipedia.org/wiki/Piroctone_olamine.*
Extended European Search Report for EP 12810815.6, 7 pages (dated Nov. 18, 2014).
International Search Report of PCT/AU2012/000841, 5 pages (dated Oct. 5, 2012).
Written Opinion for PCT/AU2012/000841, 6 pages (dated Oct. 5, 2012).

* cited by examiner

*Primary Examiner* — Terry A McKelvey
*Assistant Examiner* — Catheryne Chen
(74) *Attorney, Agent, or Firm* — Choate, Hall & Stewart LLP; Charles E. Lyon

(57) ABSTRACT

The present invention provides a disinfecting formulation useful, for example, for cleaning and disinfecting human or animal body parts, and in particular for disinfecting human hands. The disinfecting formulation comprises alcohol including ethanol; an essential oil comprising cineole, in particular eucalyptus oil; an emollient including glycerin; and other ingredients comprising piroctone olamine, acrylic acid based polymer and 2-amino-2-methyl-1-propanol. The invention also provides methods of disinfection of human and animal body parts and methods for preparing the formulation.

14 Claims, No Drawings

DISINFECTING FORMULATIONS AND USES THEREOF

FIELD OF THE INVENTION

The present invention provides a disinfecting formulation useful, for example, for cleaning and disinfecting human or animal body parts, and in particular for disinfecting human hands. The invention also provides methods of disinfection of human and animal body parts and methods for preparing the formulation.

BACKGROUND OF THE INVENTION

There is an increasing need to develop improved methods and products for cleaning and disinfecting human and animal body parts, and in particular human hands. In addition to the normal need for individuals to maintain clean and disinfected hands in order to minimise the potential for transfer of pathogens, the members of a large number of professions are required to clean their hands during the course of their normal work. For example, those involved in the provision of human health care, in the preparation of food and beverage, the handling of animals, in child and geriatric care and in cleaning and waste management will all need to ensure their hands are regularly cleaned to avoid the transmission of pathogens that may cause disease either to themselves or to others. The conventional approach for hand cleaning is to use soap and water and in many workplaces where hygiene is paramount, liquid soaps or alcohol based hand rubs (gels or foams that include denatured alcohol that has been made unpalatable for human consumption) are adopted, many of which may include antimicrobial active agents such as isopropanol, chlorhexidine, triclosan, quaternary ammonium compounds, iodinated compounds and the like or parabens, glycols and synthetic fragrances. The problem with many of these agents is that they are harsh on the skin, and in the case of the antimicrobials many microbes have mutated to develop resistance to them. It is therefore desirable to develop fast acting hand cleaning formulations that exhibit high efficiency of killing or inactivating pathogens while being relatively gentle on the skin, to thereby allow for regular use (by not only trained professionals but also the general public) without development of skin irritation, inflammation, dryness, cracking, redness or an allergic response (particularly in the case of pre- and post-operative patients). Owing to some of the additives used in conventional hand cleaning formulations, it is necessary to also use a separate barrier cream and/or skin conditioner to protect and/or rehydrate the skin. Indeed the use of a separate barrier cream and/or skin conditioner is recommended by the World Health Organisation (WHO) in its "WHO Guidelines on Hand Hygiene in Health Care" published in 2009 (the disclosures of which are included herein in their entirety by way of reference) for subject susceptible to skin irritation. It would be preferable if the additional use of such barrier creams and skin conditioners was not required. Ideally, hand cleaning formulations should neither dehydrate the skin nor cause skin irritation, inflammation, dryness, cracking, redness or an allergic response.

There are also a range of settings in which it is desirable to minimise the need for the use of water in conjunction with cleansing. In terms of daily hand cleansing this is a particular issue at the moment in parts of the world where climatic and rainfall conditions are changing and where water is becoming increasingly scarce. In parts of Australia, for example, availability of water is of increasing importance due to limits being placed at least in some areas on household water consumption. It is also desirable to have access to means of effectively cleansing for military applications or in the case of activities such as outdoor labour, camping, bushwalking and the like, where limited amounts of water may be available and where any available water will be for consumption rather than for washing.

It is in this context that the present inventors have conceived a disinfecting formulation that may be used in the absence of additional water. The inventors have adopted substantially natural products that exhibit surprising efficacy against a broad range of pathogenic microorganisms, and which can be used repeatedly on human and animal skin generally without significant irritation, inflammation, dryness, cracking, redness or allergic response. There is also no evidence of the development of microbial resistance against the formulations of the invention. Primary ingredients of the formulations according to the invention include alcohol, one or more essential oils comprising cineole and a moisturiser, which is preferably a plant derived oil. Further, although it is well understood that alcohols such as ethyl alcohol exhibit antimicrobial activity (due to their ability to denature protein) it is also understood that the effects of the alcohol do not persist on the skin due to evaporation without residue. The inventors have determined, however, that other components of the inventive formulation do leave a residue, which is not unpleasant or irritant for users, but which results in persistence of antimicrobial activity on the skin surface. Thus the formulations of the invention are useful as a professional hygienic handrub, for example for health professionals, as a surgical handrub and for preoperative skin preparation for patients about to undergo surgery. It has also been observed that the formulations of the present invention improve symptoms of skin irritation and dryness that may have been caused by the application of other cleansing formulations in some subjects.

German Patent Application No. 202007002978 discloses a gel composition comprising specified amounts of alcohol, thickener, at least one active agent selected from sedatives, healing promoters and/or anti-inflammatory agents, as well as water. For effective disinfection activity this formulation appears to require the presence of biguanide compounds, phenol compounds, iodine compounds or the like, which are not required for disinfection in the present invention. In preferred embodiments of the present invention such compounds are excluded from the formulation according to the present invention, such that disinfecting activity is contributed to by essential oils and alcohol.

International Patent Publication No. WO 2005/084717 discloses a cleaning solution comprising ethanol, and essential oil with specified content of cineole. While the cleansing and disinfecting properties of alcohol such as ethanol and essential oils comprising cineole were understood, it was not expected that such agents could be combined into an alcohol based hand rub (ABHR) formulation that has moisturising properties. Before the work of the present inventors it was generally understood that it was not possible to effectively moisturise using such formulations without either compromising upon anti-microbial effectiveness or requiring the need for the inclusion of irritant anti-microbial agents such as quaternary ammonium compounds, chlorhexidine or chlorhexidine gluconate, chloroxylenol, benzalkonium chloride, fluorosalan, hexachlorophene, phenol, tribromosalan, triclocarban, triclosan and isopropanol. Indeed WHO notes in its Guideline referred to above that hand rub formulations should contain 1% to 2% of moisturiser and that adding more than 3% of moisturiser can compromise antimicrobial activity.

SUMMARY OF THE INVENTION

In one aspect of the invention there is provided a disinfecting formulation comprising:
(a) alcohol;
(b) one or more essential oils comprising cineole; and
(c) an emollient.

In another aspect the present invention relates to a disinfecting formulation for topical application to human or animal skin comprising:
(a) ethanol;
(b) eucalyptus oil;
(c) glycerine;
(d) piroctone olamine; and
(e) water.

In another aspect the present invention relates to a disinfecting formulation for topical application to human or animal skin comprising:
(a) ethanol;
(b) eucalyptus oil;
(c) glycerine;
(d) terpinen-4-ol;
(e) piroctone olamine; and
(f) water.

In another aspect the present invention relates to a disinfecting formulation for topical application to human or animal skin comprising:
(a) ethanol;
(b) eucalyptus oil;
(c) glycerine;
(d) piroctone olamine; and
(e) water.

In another aspect the present invention relates to a disinfecting formulation for topical application to human or animal skin comprising:
(a) ethanol;
(b) eucalyptus oil;
(c) glycerine;
(d) acrylic acid based polymer; and
(e) water.

In another aspect the present invention relates to a disinfecting formulation for topical application to human or animal skin comprising:
(a) ethanol;
(b) eucalyptus oil;
(c) glycerine;
(d) acrylic acid based polymer;
(e) 2-amino-2-methyl-1-propanol; and
(f) water.

In a preferred embodiment the formulations referred to above are applied to human skin.

Preferably the formulation comprises one or more $C_1$ to $C_{10}$ alcohol, preferably one or more of methanol or ethanol. It is particularly preferred that the alcohol comprises ethanol of analytical grade (A.R).

Preferably the one or more essential oils is selected from eucalyptus, tea tree, bayleaf, spearmint and rosemary oils, preferably eucalyptus oil and most preferably eucalyptus oil of B.P. (British Pharmacopoeia) grade. In an embodiment the formulation may optionally comprise tea tree oil or tea tree oil extract such as terpinen-4-ol.

In an embodiment the emollient is or comprises one or more of lanolin, mineral, vegetable and synthetic oils and humectants. For example, humectants may include glycerine, propylene glycol, glyceryl triacetate, sorbitol, xylitol, melitol and polydextrose and vegetable oils may comprise coconut oil, jojoba oil, shea butter, mango butter and palm oil. Preferably the emollient is glycerine (glycerol) and preferably it is plant derived glycerine.

In another embodiment where the formulation is a hand gel where the formulation comprises one or more gelling or thickening agents.

In one embodiment the formulation comprises, by volume, from about 60% to about 80% ethanol, from about 5% to about 15% eucalyptus oil and from about 2% to about 10% glycerine.

In another embodiment of the invention there is provided a disinfecting formulation comprising, by volume:
(a) from about 60% to about 80% ethanol;
(b) from about 5% to about 15% eucalyptus oil;
(c) from about 2% to about 10% glycerine;
(d) from about 0.01% to about 0.1% piroctone olamine; and
(e) water.

In another embodiment of the invention there is provided a disinfecting formulation comprising, by volume:
(a) from about 60% to about 80% ethanol;
(b) from about 5% to about 15% eucalyptus oil;
(c) from about 2% to about 10% glycerine;
(d) from about 0.1% to about 1% terpinen-4-ol;
(e) from about 0.01% to about 0.1% piroctone olamine; and
(f) water.

In another embodiment the formulation comprises, by volume:
(a) about 73% of 95% ethanol;
(b) about 10% eucalyptus oil;
(c) about 5% glycerine;
(d) about 0.5% terpinen-4-ol;
(e) about 0.05% piroctone olamine; and
(f) water.

In another embodiment of the invention there is provided a disinfecting formulation comprising, by volume:
(a) from about 60% to about 80% ethanol;
(b) from about 5% to about 15% eucalyptus oil;
(c) from about 2% to about 10% glycerine;
(d) from about 1% to about 2% acrylic acid based polymer; and
(e) water.

In another embodiment of the invention there is provided a disinfecting formulation comprising, by volume:
(a) from about 60% to about 80% ethanol;
(b) from about 5% to about 15% eucalyptus oil;
(c) from about 2% to about 10% glycerine;
(d) from about 1% to about 2% acrylic acid based polymer; and
(e) from about 0.8% to about 2% 2-amino-2-methyl-1-propanol; and
(f) water.

The invention also includes a method of disinfecting a human or animal body part comprising applying to the body part a formulation as defined above.

In one embodiment there is provided a method of disinfecting a human or animal body part comprising applying to the body part a formulation comprising, by volume:
(a) from about 60% to about 80% ethanol;
(b) from about 5% to about 15% eucalyptus oil;
(c) from about 2% to about 10% glycerine;
(d) from about 0.1% to about 1% terpinen-4-ol;

(e) from about 0.01% to about 0.5% piroctone olamine; and
(f) water.

In another embodiment the formulation used in the method comprises, by volume:
(a) about 73% of 95% ethanol;
(b) about 10% eucalyptus oil;
(c) about 5% glycerine;
(d) about 0.5% terpinen-4-ol;
(e) about 0.05% piroctone olamine; and
(f) water.

In another embodiment there is provided a method of disinfecting a human or animal body part comprising applying to the body part a formulation comprising, by volume:
(a) from about 60% to about 80% ethanol;
(b) from about 5% to about 15% eucalyptus oil;
(c) from about 2% to about 10% glycerine;
(d) from about 0.01% to about 0.1% piroctone olamine; and
(e) water.

In one embodiment the method is for disinfecting human hands and in another embodiment the formulation is for pre-operative treatment disinfection of human skin.

In another embodiment there is provided a method of disinfecting a human or animal body part comprising applying to the body part a formulation comprising, by volume:
(a) from about 60% to about 80% ethanol;
(b) from about 5% to about 15% eucalyptus oil;
(c) from about 2% to about 10% glycerine;
(d) from about 1% to about 2% acrylic acid based polymer; and
(e) water.

In another embodiment there is provided a method of disinfecting a human or animal body part comprising applying to the body part a formulation comprising, by volume:
(a) from about 60% to about 80% ethanol;
(b) from about 5% to about 15% eucalyptus oil;
(c) from about 2% to about 10% glycerine;
(d) from about 1% to about 2% acrylic acid based polymer; and
(e) from about 0.8% to about 2% 2-amino-2-methyl-1-propanol; and
(f) water.

DETAILED DESCRIPTION OT THE INVENTION

The reference to any prior art in this specification is not, and should not, be taken as an acknowledgment or any form of suggestion that the prior art forms part of the common general knowledge in Australia.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

Throughout this specification and the claims which follow, unless the context requires otherwise, the phrase "consisting essentially of", and variations such as "consists essentially of" will be understood to indicate that the recited element(s) is/are essential i.e. necessary elements of the invention. The phrase allows for the presence of other non-recited elements which do not materially affect the characteristics of the invention but excludes additional unspecified elements which would affect the basic and novel characteristics of the method defined.

In a preferred embodiment, the disinfecting formulation comprises alcohol such as a $C_1$ to $C_{10}$ alcohol, preferably selected from one or more of methanol or ethanol. The alcohol should be non-toxic to animals and especially humans on the basis of dermal contact, and inhalation exposure since with normal use the formulation will come into contact with skin and its vapour will be inhaled. It is preferred that the alcohol is not denatured and it is particularly preferred that the alcohol is ethanol of analytical grade (A.R). Preferably the formulation includes alcohol in an amount by volume of from about 30% to about 85% (% v/v), preferably from about 60% to about 80%, more preferably from about 70% to about 75% and most preferably about 72% or about 73%. In a preferred embodiment the formulation does not include isopropanol.

The formulation comprises one or more essential oils and/or fractions thereof comprising cineole, which are generally obtained from distillation of fresh, dried or partially dried plants or plant derived materials. The essential oil may be obtained from components such as leaves, branches, shoots, stems, bark, seeds, fruit, roots, nuts or the like from one or more plants. Essential oil fractions may be obtained from distillation, purification, refining or the like of essential oils or components thereof. The essential oils and/or fractions are preferably selected from the group eucalyptus, tea tree, bayleaf, spearmint and rosemary oils, although other plant species may also give rise to essential oils containing cineole compounds, preferably 1,8-cineole, and preferably in an amount of 20% to 100% of the oil. In a still further preferred embodiment, eucalyptus oil of B.P. grade (where it complies with British Pharmacopoeia requirements) is used and preferably a visibly clear grade is used so as to produce a clear formulation, which is generally more aesthetically appealing to consumers. Preferably the amount by weight of cineole in the essential oil, preferably eucalyptus oil, is at least about 60% (% v/v), preferably from about 75% to about 85%. In a preferred embodiment, the amount by volume of the essential oil, preferably eucalyptus oil, within the formulation is from about 5% to about 30%, preferably from about 10% to 25%, more preferably from about 10% to about 15% and most preferably about 10% or about 11%.

The formulations may also include tea tree oil or an extract of tea tree oil, such as terpinen-4-ol, which is commercially available and is understood to be the primary active agent of tea tree oil. The presence of tea tree oil or an extract thereof in the formulation has been demonstrated by the inventors to assist with preservation of the formulation, to make the formulation unpalatable for human consumption (which is necessary in some jurisdictions for regulatory purposes if a non-denatured alcohol is used, as is preferred) and contributes to antimicrobial activity, particularly due to leaving a residue on the skin (which is not unpleasant or irritant) that improves persistence of the antimicrobial activity. The structure of terpinen-4-ol is as follows:

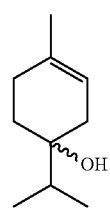

Terpinen-4-ol chemical structure

If present, the tea tree oil, extract thereof or terpinen-4-ol can be present in an amount of from about 0.1% to about 1% v/v, preferably from about 0.2% to about 0.8% and preferably about 0.5% v/v.

The formulations of the invention also include water. Preferably the water will be UV light treated or purified to remove pathogens such as by microfiltration and/or distillation. The formulation includes water in an amount by volume of from about 5% to about 20% (% v/v), preferably from about 5% to about 15%, preferably from about 10% to about 15%, such as about 10%, about 11%, about 12%, about 13%, about 14% or about 15%.

A preferred further ingredient in some embodiments of the invention which are formulated to produce a hand rub (ABHR), is piroctone olamine (1-Hydroxy-4-methyl-6-(2,4, 4-trimethylpentyl)-2(1H)-pyridone in combination with 2-aminoethanol (1:1); also known as Octopirox®) which is commercially available from Clariant and is extensively used in hair care formulations as an anti-dandruff agent. It is also an anti-oxidant that has been shown to exhibit antimicrobial activity against a range of pathogens, including Gram-positive and Gram-negative bacterial and fungi. It is derived form organic salts using green chemistry. Without wishing to be bound by theory, it appears that in the present invention the presence of piroctone olamine not only assists in the preservation of the formulation by acting as a pH buffer but also contributes to sustained anti-microbial action. In relation to the former advantage, it has been found that previous formulations encountered marked decreases in pH over their shelf life which in turn negatively impacts on antimicrobial performance. It has now been shown that the addition of piroctone olamine stabilises the pH of formulations which in turn enhances the antimicrobial effects of the formulation over an increased shelf life time. The piroctone olamine will generally be present in the formulation in an amount of from about 0.01% to about 0.5% by volume, preferably from about 0.02% to about 0.1% or about 0.05% v/v, and preferably about 0.02%, 0.03%, 0.04% or about 0.05% v/v. It is also postulated that the combination of, for instance, eucalyptus oil and piroctone olamine may provide for a persistent or sustained anti-microbial effect on the surface of the skin. In this way it is postulated that this increased anti-microbial residence time or prolonged antimicrobial effect may be created through a synergistic inter-relationship with, for instance, eucalyptus oil and piroctone olamine. As a further advantage it has been found that the piroctone olamine decreases the usually noticeable smell of the eucalyptus oil which makes the overall aroma of the formulation more pleasant.

The formulation may also include one or more emollient agents which serve to soften the skin, usually by improving skin hydration (i.e. moisturising the skin). Examples of suitable emollients are lanolin, mineral, vegetable and synthetic oils and humectants. Humectants are hygroscopic agents that have the ability to form hydrogen bonds and attract water to thereby have a moisturising effect. For example, humectants may comprise glycerine, propylene glycol, glyceryl triacetate, sorbitol, xylitol, melitol and polydextrose. Examples of vegetable oils include coconut oil, jojoba oil, shea butter, mango butter and palm oil. The emollients utilised should all be non-toxic in dermal use and substantially non-irritant and non-allergenic.

Preferably the emollient will be present in an amount by volume of from about 2% to about 10%, preferably from about 3% to about 8% and more preferably from about 4% to about 6%, such as about 5% v/v. In a particularly preferred embodiment the emollient agent is glycerine, preferably vegetable glycerine which is readily commercially available, and which may be present in an amount by volume as mentioned above.

In another embodiment the invention provides a disinfecting formulation consisting of, by volume:
(a) from about 60% to about 80% ethanol;
(b) from about 5% to about 15% eucalyptus oil;
(c) from about 2% to about 10% glycerine;
(d) from about 0.01% to about 0.1% piroctone olamine; and
(e) water.

In another embodiment the invention provides a disinfecting formulation consisting essentially of, by volume:
(a) from about 60% to about 80% ethanol;
(b) from about 5% to about 15% eucalyptus oil;
(c) from about 2% to about 10% glycerine;
(d) from about 0.01% to about 0.1% piroctone olamine; and
(e) water.

The above embodiments which exclude thickeners (gelling agents) may be beneficially used as handrubs, for instance, in a surgical setting where a sustained antimicrobial effect is required.

In relation to the above two embodiments this includes a method of disinfecting a human or animal body part (preferably human) comprising applying to the body part a formulation as defined above. It will be appreciated that in the context of the above embodiment "consisting essentially of" will exclude the use of additional emollients (other than glycerine), further disinfectant agents, thickeners (gelling agents), but may include small amounts of pH adjusting agents such as, for instance, lactic acid, (i.e. for instance in an amount of from 0.02%-0.2% v/v).

In other embodiments of the invention additional ingredients not otherwise specified may be included within the formulation such as for example essential oils that do not include cineole, to any significant extent (e.g. clove oil, sweet orange oil), other agents active against microorganisms, aromatic scents, stabilisers, preservatives and the like that are routinely used in dermal preparations, which should all be non-toxic in dermal use and substantially non-irritant and non-allergenic. Preferably such agents are naturally derived.

In another embodiment where the formulations are intended to be used as handgels they may additionally comprise one or more gelling agents in an amount suitable to modify the formulations into a gelled state. Preferably the gel is in a form that allows it to be readily dispensed, for example from a tube, tub or pump pack, and can be easily spread upon the surface to be disinfected. By reference to a gel it is intended to convey that there is formation of a colloid that is to some extent immobilised and exhibits solid or semi-solid characteristics. Gelling agents that serve to thicken or impart a level of structural form to the formulation such as vegetable, animal, mineral, petroleum or synthetic waxes, vegetable gums, starches, pectins, gelatine, chitin, chitosan, collagen, silica, cornstarch, glycols and carbomer (polyacrylic acid) can be used. For example, vegetable gums include locust bean gum, guar gum, xanthan gum, alginates, agar, carageenan, beta-glucan, gellan gum, gum arabic, gum tragacanth, karaya gum, locust bean gum, mastic gum, psyllium gum, spruce gum, ghatti gum and glucomannan and vegetable, animal, mineral, petroleum or synthetic waxes include beeswax, shellac wax, spermaceti, lanolin, bayberry wax, candelilla wax, carnauba wax, castor wax, esparto wax, jojoba oil, ouricury wax, rice bran wax, soy wax, ceresin waxes, montan wax, ozocerite, paraffin wax, microcrystalline wax, polyethylene waxes, chemically modified waxes, Fischer-Tropsch waxes, substituted amide waxes and polymerised α-olefins. To be useful within the formulations of the present invention the gelling agents should be non-toxic in dermal use and substantially non-irritant and non-allergenic. The gelling agents may be present in amounts by volume of from about 0.1% to about 5%, preferably from about 0.5% to about 3% and more preferably from about 1% to about 2%, for instance, 1.1%, 1.2%, 1.3%, 1.4%, 1.5%, 1.6%, 1.7%, 1.8%, or 1.9%.

In an embodiment the gelling agents are petroleum waxes, examples of which include paraffin wax and microcrystalline wax. A preferred petroleum wax is the proprietary formulation known as "Anhydro Wax", which is commercially available from Intelisol Pty Ltd of 1/57 Malvern Street, Bayswater, Victoria, 3153, Australia. If "Anhydro Wax" is adopted in the formulation it is preferably used in an amount by volume of from about 0.5% to about 2%, preferably from about 1% to about 2% or preferably about 1.5%. Another preferred gelling agent is polymeric sulfonic acid, which may be partially neutralised with ammonia, such as the Aristoflex™ product available from Clariant, Frankfurt, Germany.

In a preferred embodiment the formulation comprises a gelling or thickening agent which is an acrylic acid based polymer such as Carbopol® or Pemulen®. Carbopol® and Pemulen® are high molecular weight homo- and copolymers of acrylic acid crosslinked with a polyalkenyl polyether. Preferably the acrylic acid based polymer is present in conjunction with a neutralising agent which may be an organic base. Preferably the base is 2-amino-2-methyl-1-propanol. More preferred the base is 95% 2-amino-2-methyl-1-propanol. Preferably the base is added in an amount of about 0.8%-about 2% v/v of the formulation. Preferably the gelling or thickening agent is Carbopol, and preferably in an amount of about 1% to about 2% v/v, such as about 1.1%. The present formulation presented as a gel has the added advantage of being able to dry quicker than conventional gels which is important in clinical settings. The drying time has been noted to be around 25-40 seconds, and on average 30 seconds. Conventional gels can take much longer, for instance, up to 1 minute.

In a preferred embodiment the gelling or thickening agent is added to achieve viscosity of from 5,000-8,000 cps, and preferably about 6,000-7,000, and more preferably about 6,000 cps.

In a preferred embodiment the pH of any of the formulations referred to herein is from about 4.5 to 8.5, such as from about 6-8.5.

In a further embodiment the formulation is about 8, such as within the range 7.8-8.5.

The formulation is a disinfectant in that it has anti-microbial activity and hence will kill, slow growth and/or cellular division of microorganisms and other pathogens such as bacteria (Gram positive and Gram negative), viruses, fungi, protozoa, mites, algae, nematodes and the like (collectively referred to as "flora"). By application of the solution to the skin preferably at least 90%, more preferably at least 95%, particularly preferably at least 98% or 99% and most preferably at least 99.5% or 99.9% of flora on the skin will be killed or otherwise inactivated. The superior disinfecting nature of the preferred formulation of the invention (comprising aqueous ethanol, eucalyptus oil, glycerine, and piroctone olamine) is attributed to the prolonged presence of ethanol on the skin and persistence of a non-irritant residue of eucalyptus oil, and piroctone olamine. It is further postulated that upon application of the formulation, the eucalyptus oil and glycerine components act to delay evaporation of the ethanol component, thereby allowing the ethanol component to kill any flora present on the skin and prevent regrowth for an extended period of time. In contrast, conventional disinfecting formulations contain hazardous chemicals to achieve such persistent anti-microbial activity.

In an embodiment the formulation provides a Log reduction of at least 4.0, about 10-15 seconds after application.

In an embodiment the formulation provides a Log reduction of at least 4.0, about 15-30 seconds after application.

In an embodiment the formulation provides a Log reduction of at least 4.0, about 30-60 seconds after application.

In an embodiment the formulation provides a Log reduction of at least 4.0 for at least about 30 minutes.

In an embodiment the formulation provides a Log reduction of at least 4.0 for at least about 1 hour.

In an embodiment the formulation provides a Log reduction of at least 4.0 for at least about 2 hours.

In a further embodiment the formulation provides a Log reduction of at least 4.0 for at least about 3 hours.

In a further embodiment the formulation provides a Log reduction of at least 4.0 for at least about 4 hours.

The formulation will be physiologically compatible with skin. In addition to disinfecting, the formulation may assist to clean skin (by removing dead skin cells, grease, grime and the like) and/or manage minor wounds and skin disorders (e.g., cuts, scratches, abrasions, eczema, dermatitis, tinea, fungal skin disorders, acne, herpes sores). The formulation can also symptomatically assist with management of minor wounds, abrasions, infections, insect bites, stings, sun burn and minor skin burns. It can be used as a treatment or preventative against tinea/athletes foot.

The formulation sooths itchy sore red skin, conditions noted in people that have eczema. The formulation kills polyps/herpes, and when applied does not dry and crack the skin. The formulation demonstrates high anti toxic resistance due to its natural chemistry. For instance, the formulation may be used to treat insect bites in which the bite contains toxins. Applying the formulation quickly may counter attack the toxins/infection and heal the skin quickly.

The formulation can, for example, be dispensed from a pump container, spray container canister, tub or tube, or alternatively a single dose of the formulation may be provided in a sealed foil or laminated plastic (polypropylene) sachet. In a preferred embodiment when the formulation is a hand rub it has a viscosity which allows it to be readily sprayable, such as, for instance 7 to 100 cps. It can be provided on or with swabs for skin cleansing or in sealed packaging with sponges for surgical theatre use. In use an amount sufficient to coat the hands or skin to be cleansed will be applied to the skin. The formulation is a "leave on" application and dries naturally. However, excess formulation may be removed by wiping with paper towel or a dry cloth (which should be sterile in the case of medical/surgical applications).

The disinfecting formulation of the invention can, for example, be prepared by adding aqueous ethanol to a stainless steel mixing container and then adding the preservative (if present) with mixing to aid dissolution. Eucalyptus oil and emollient are then separately added with thorough mixing, with subsequent addition of tea tree oil or an extract of tea tree oil, if present. The mixture is then made up to the desired volume with purified water.

The present invention will now be described further with reference to the following non-limiting examples:

EXAMPLES

Example 1—Preparation of Disinfecting Formulation

A formulation (hand rub) was prepared containing the ingredients listed in Table 1 below in the percentage amounts by volume as indicated.

TABLE 1

| |
|---|
| 73% A.R. grade aqueous ethanol (95% v/v) |
| 10% B.P. grade *eucalyptus* oil |
| 5% plant derived glycerine |
| 0.5% terpinen-4-ol |
| 0.05% piroctone olamine |
| distilled water up to volume |

The formulation was prepared by adding 43.8 kg of the ethanol solution to a stainless steel mixing container and then adding 0.03 kg of piroctone olamine with mixing to aid dissolution. Eucalyptus oil (6 kg) and glycerine (3 kg) were each then separately added with thorough mixing, with subsequent addition of 0.3 kg of the terpinen-4-ol. The mixture was then made up to 60 L with purified water.

Example 2

A formulation (hand rub) was prepared containing the ingredients listed in Table 1a below in the percentage amounts by volume as indicated.

TABLE 1A

| RAW INGREDIENT COMPONENT | Theoretical 1.000 (% V/V) | SG | Actual 1.000 (% W/V) | Test 4.000 (% W/V) |
|---|---|---|---|---|
| Purified Water | 12.03 | 1.000 | 12.03 | 48.13 |
| Glycerol BP | 5.00 | 1.262 | 6.31 | 25.24 |
| Octopirox | 0.05 | 1.000 | 0.05 | 0.20 |
| Total Phase 1 Materials | 5.05 | | 6.36 | 25.44 |
| Ethanol, Undenatured 96% BP | 72.92 | 0.809 | 58.95 | 235.81 |
| *Eucalyptis* Oil BP | 10.00 | 0.917 | 9.17 | 36.66 |
| Total Phase 2 Materials (Target pH: 8.1) | 82.92 | | 68.12 | 272.47 |
| Total Units | 100.000 (%) | | 86.511 Grams per 100.0 ML | 346.046 Grams per 400.0 ML |

Instruction:
Note: All Materials to be at Room Temperature
1). Add Phase 1 materials in the main mixing vessel in the stated order. Mix moderately until all materials have been dissolved
2). Slowly add phase 2 into main vessel. Mix each component into the batch with an air mixer until homogeneous.
3). Mix for 15 minutes. Adjust with Lactic Acid to target pH value of 8.1. Mix for an additional 10 minutes.

RELEASE SPECIFICATION
Release Specifications for the Formulated Gel Product

| Test Parameter | Test Method | Specification |
|---|---|---|
| Identification of Ethanol | Gas Chromatography | Retention time of the sample matches the retention time of the standard |
| Ethanol Content | Gas Chromatography | 6.5%-7.5% (v/v) |
| Appearance & Colour | Visual | Clear liquid with a very slight yellow tinge |
| Odour | Sensory | *Eucalyptus* scent |
| pH | Potentiometry | 6.0-8.5 |
| Bacterial Count | TGA Topical Liquid Test | <10 CFU/g |
| Yeast and Mould Count | TGA Topical Liquid Test | <10 CFU/g |
| *Staphylococcus aureus* | TGA Topical Liquid Test | None in 1 g |
| *Pseudomonas* | TGA Topical Liquid Test | None in 1 g |

Example 3

A formulation (hand gel) was prepared containing the ingredients listed in Table 1b below in the percentage amounts by volume as indicated.

TABLE 1b

| RAW INGREDIENT COMPONENT | Theoretical 1.000 (% V/V) | SG | Actual 1.000 (% W/V) | Test (% W/V) |
|---|---|---|---|---|
| Purified Water | 11.13 | 1.000 | 11.13 | 22.26 |
| Glycerol BP | 4.00 | 1.262 | 5.05 | 10.10 |
| Ethanol, Undenatured 96% BP | 72.92 | 0.809 | 58.95 | 117.91 |
| Carbopol Ultrez 20 | 1.05 | 1.000 | 1.05 | 2.10 |
| Total Phase 1 Materials | 77.97 | | 65.05 | 130.10 |
| AMP PC-2000 | 0.90 | 0.942 | 0.85 | 1.70 |
| *Eucalyptus* Oil BP (A) | 10.0 | 0.917 | 9.17 | 18.33 |
| Total Phase 2 Materials (To pH: 6.5-7.5) | 10.90 | | 10.02 | 20.03 |
| Total Units | 100.000 (%) | | 86.197 Grams per 100.0 ML | 172.395 Grams per ML |

INSTRUCTION:
NOTE:
all materials to be at room temperature
1). Add Phase 1 materials in the main mixing vessel in the stated order. Mix moderately until all carbopol have been dissolved
2). Add Phase 2 into main vessel and mix for 30 minutes.

RELEASE SPECIFICATION
Release Specifications for the Formulated Gel Product

| Test Parameter | Test Method | Specification | Test Site |
|---|---|---|---|
| Identification of Ethanol | Gas Chromatography | Retention time of the sample matches the retention time of the standard | ALS Melbourne |

-continued

RELEASE SPECIFICATION
Release Specifications for the Formulated Gel Product

| Test Parameter | Test Method | Specification | Test Site |
|---|---|---|---|
| Ethanol Content | Gas Chromatography | 65%-75% (v/v) | ALS Melbourne |
| Appearance & Colour | Visual | Clear gel with slight yellow to off white tinge | Baxter Laboratories |
| Odour | Sensory | *Eucalyptus* scent | Baxter Laboratories |
| Viscosity | spRV4/10 (20° C.) | 2000-6500 cps | Baxter Laboratories |
| pH | Potentiometry | 7.0-7.5 | Baxter Laboratories |
| Bacterial Count | TGA Topical Liquid Test | <10 CFU/g | EML Melbourne |
| Yeast and Mould Count | TGA Topical Liquid Test | <10 CFU/g | EML Melbourne |
| *Staphylococcus aureus* | TGA Topical Liquid Test | None in 1 g | EML Melbourne |
| *Pseudomonas* | TGA Topical Liquid Test | None in 1 g | EML Melbourne |

Example 4—Test Against Surgical Handrub Standard

Objective

To determine whether the disinfecting formulation produced according to the protocol of Example 1 meets the European standard for a surgical handrub (EN 12791 of 2005), which requires a significant log reduction in hand microflora both immediately and over a 3 hour sustained period, when compared against a standard formulation (60% propan-1-ol).

Test Protocol

The protocol is based upon European standard EN 12791: 2005 designed for testing "Chemical disinfectants and antiseptics—Surgical hand disinfectant".

The clean and healthy hands (free of cuts and abrasions and with short, clean fingernails) of 5 volunteers were initially washed for 1 min with soap and water and dried with paper towel. To establish base line flora levels the fingertips and thumb were rubbed for 1 minute on the base of a petri dish containing 10 ml of Tryptone Soy Broth (TSB). A separate petri dish was used for each hand. Dilutions of $10^{-2}$ and $10^{-3}$ were prepared from the TSB that were assayed by the pour-plate method using Tryptone Soy Agar (TSA) plates. The time between sampling and plating did not exceed 30 mins.

Immediately after sampling for the baseline and without recontamination of the hands the subjects performed the handrub test. The subjects were split into two groups which were alternately treated with the standard formulation or the test formulation initially and then the other formulation, separately by a week to allow re-colonisation of native flora.

The handrub test involved the hands of each volunteer being exposed to treatment with two 4.6 ml aliquots of both the test and standard formulations. The treatment involved an initial application of the formulation (test or standard) for 30 seconds and then immediate further treatment for a further 30 seconds for a total exposure in each case of 60 seconds.

The finger tip and thumb of the left hand were then rubbed for 1 min on the base of a petri dish containing 10 ml of PDE neutraliser to provide the immediate effect results. The right hand was covered by a sterile glove for 3 hours, followed by the same testing protocol for the left hand, to provide the sustained effect results.

The test plates were diluted $10^0$ and $10^{-1}$ and were exposed to the pour-plate assay using TSA. All plates were incubated for 18 to 24 hours at 36° C.±2° C.

$Log_{10}$ values for immediate effect and sustained effect were then determined and a Log Reduction Factor for both test formulation and standard formulation were calculated based on the average difference between the $log_{10}$ pre-value and the $log_{10}$ post-value in each subject.

Results

The standard formulation reduced hand microflora by 1.61 Logs immediately and 1.89 Logs after 3 hours, whereas the test formulation reduced hand microflora by 1.61 Logs immediately and 2.02 Logs after 3 hours. The test formulation was therefore more effective than the standard formulation and meets the requirements of the EN 12791 standard.

Example 5—Test Against Hygienic Handwash Standard

Objective

To determine whether the disinfecting formulation produced according to the protocol of Example 1 meets the European standard for a hygienic handwash (EN 1500 of 1997), which requires a significant log reduction in hand contaminant bacteria for artificially contaminated hands, when compared against a standard formulation (60% propan-1-ol).

Test Protocol

The protocol is based upon European standard EN 1500: 1997 designed for testing "Chemical disinfectants and antiseptics—Hygienic handwash".

The subjects (15 volunteers with clean and healthy hands that were free of cuts and abrasions and having short, clean fingernails) were split into two approximately equal groups which were alternately treated with the standard formulation or the test formulation initially and then the other formulation, separately by a one day.

The hands of the subjects were initially washed for 1 min with soap and water and dried with paper towel. The contamination fluid (*Escherichia coli* (NCTC 10538) bacterial suspension of between $2\times10^8$ and $2\times10^9$ cfu/mL) was placed into a tray and each subject immersed his/her hands up to the mid-metacarpals for 5 seconds. Excess fluid was allowed to drain back into the container. Hands were air dried for 3 minutes, holding them in a horizontal position. Each subject was encouraged to rotate their hands to avoid the formation of droplets. Each subject was treated from the same batch of contamination fluid.

After drying, fingertips and thumb were rubbed for 1 minute on the base of a Petri-dish, which contained 10 mL of TSB. A separate Petri-dish for each hand (Left and Right) was used. This was the Pre-value. Dilutions of $10^{-4}$ and $10^{-5}$ were prepared using sterile Peptone Water (PEP). Each dilution was spread onto pre-poured, dried TSA plates. The time between sampling and plating did not exceed 30 minutes. Immediately after sampling for the pre-values and without re-contaminating the hands, the group performed the 'handwash' procedure, initially with either test formulation or standard formulation, with the standard formulation being applied to Group 1 volunteers on Day 1 and Group 2 volunteers on Day 2 and the test formulation being applied to Group 1 on Day 2 and Group 2 on Day 1.

For the standard formulation, 3 mL of 60% propan-2-ol was dispensed onto the subject's hands and rubbed over for 30 seconds using the standard procedure as instructed. This was done twice to give total of 6 mL of 60% propan-2-ol over a 60 second rub. This procedure was completed with a 5 second rinse of fingers under running tap water.

For the test formulation, 3 mL of test product was dispensed onto the subject's hands and rubbed over for 30 seconds using the standard procedure as instructed. This was done twice to give total of 6 mL test product over 60 second rub. The test product procedure was completed with a 5 seconds rinse of fingers under running tap water.

The Post-value was obtained by rubbing the fingertips and thumb on the base of a Petri-dish containing 10 mL of either T6 or PDE Broth as inactivating agent (dilution of $10^0$). Dilutions of $10^0$, $10^{-1}$ and $10^{-2}$ were spread on pre-poured and dried TSA plates. All plates were incubated at 36° C.±2° C. for 24-48 hours.

Results and Calculations

After the incubation period, all the plates were checked and colony forming units on both standard and test sample were counted. Dilutions with counts that are within 15-300 cfu were used in the computation. Plates showing less than 15 cfu or no growth were also counted.

Data were collected from 15 volunteers, but only 14 were taken into account as the results of plate count from one subject were evidently improbable and hence excluded. With 14 subjects, the test remains in compliance with the minimum requirement of 12. No other deviation to the experimental protocol was required.

To meet the requirements of EN 1500 all results from at least 12 subjects shall be available and the overall mean of the log prevalues for the standard and test product shall be at least 5.00. In this study, the mean was 7.13 and 7.01 respectively. Further, in each procedure there must not be more than three subjects with log reduction factor lower than 3.00. In this study, the lowest log reduction recorded was 3.94.

It is also necessary for the mean log reduction factor obtained not to be significantly smaller than that of the standard (propan-2-ol). In this study, the mean log reduction for the test formulation is higher than that of the standard formulation, with a mean difference of 0.54.

The log reduction of contaminant bacteria of the test formulation by 5.7 may be regarded as comparable, albeit close, having surpassed that of the standard formulation (5.16 logs).

The requirements of EN 1500 have been fulfilled by the test formulation of Example 1.

Example 5a

Objective/Summary

This study was designed to evaluate the efficacy of Example 2 by the European Standard—EN 1500:1997. In this in-vivo test, the product in the recommended volume, time and frequency has achieved an average of 5.70 log reduction of the test organism, *Escherichia coli* (NCTC 10538), as opposed to the average log reduction of 5.16 from the application reference material 60% (v/v) propan-2-ol. From statistical analysis of data obtained, Example 2 can be considered as effective having shown a significantly higher log reduction than that of the reference solution propan 2-ol, as well as demonstrated compliance to all other parameters as specified in the guidelines.

Product Under Evaluation

Antimicrobial Handrub, in 250 mL containers, Batch No. BE079, was received on Aug. 4, 2011. Testing commenced 13 Apr. 2011.

Application Details:
  Volume 3.0 mL
  Contact Time: 30 seconds
  Frequency of application: twice Volunteers Fifteen individuals (volunteers) were recruited whose 'hand-skin' were healthy, without cuts or abrasions and with short and clean fingernails.

All volunteers are asked to sign a consent form and specify their age range. All volunteers should be at least 18 years of age or older.

No restriction was applied in terms of gender distribution/selection.

Materials

Culture Strain:

The test culture used in this study was obtained from the University of New South Wales Culture Collection—*Escherichia coli* (NCTC 10538)

Reagents and Suppliers:
  Tryptone Soy Broth (TSB) was supplied by Oxoid Pty. Ltd.
  Tryptone Soy Agar (TSA) was supplied by Oxoid Pty. Ltd.
  0.1% Peptone Water (PEP), supplied by Oxoid Pty. Ltd.
  T6 Broth, prepared within ams Laboratories.
  PDE Broth, prepared within ams Laboratories.
  Propan-2-ol, supplied by BDH.
  Tween 80, supplied by Spectrum Distributor.
  Soft Soap, 200 g/L per EN 1500:1997, prepared within ams Laboratories Equipment and Apparatus
  Incubator 36° C.±2° C.
  Thermometer
  Timer Jadco, supplied by Biolab.
  Pipettors and sterile pipette tips were supplied by Biolab.
  7.3.5. Sterile spreaders were supplied by Biolab.
  Sterile bottles
  Petri Plates (90 mm), sterile
  Stainless tray deep enough to immerse hands to midmetacarpals.

Methods

Neutralization Study

A neutralizer validated according to prEN 12054 were incorporated in the sampling fluids and diluents for the assessment of post-values in both test and reference procedure. PDE Broth and T6 were found to be a suitable neutralizer for test products and reference respectively.

Inoculum Preparation

The test organism was freshly revived from frozen protect beads by sub culturing in two McCartney bottles containing 5 mL of TSB. They were incubated at 37° C. These cultures are then inoculated into two bottles containing 1 L TSB. They were incubated at 37° C. for 18-24 hours The cultures were pooled into a sterile bottle to prepare the bacterial suspension. The suspension prepared in this way should be between $2\times10^8$ and $2\times10^9$ cfu/mL.

Test Procedures

For testing this product, a cross-over design was used. The subjects were randomly divided into two groups of approximately the same size. The test was first performed with Group 1 applying the reference handrub (60% Propan-2-01) and Group 2 applying the test sample and following the handrub operation as demonstrated in the guidelines. The test was then repeated on the next day with the two groups switching over the test sample and reference solution.

Establishing Pre-Values

Each subject/volunteer washed hand to remove normal dirt and natural flora using the soft soap for 1 min. The hands were then dried thoroughly on paper towels.

The contamination fluid (test suspension) was placed into the tray and each subject immersed his/her hands up to the mid-metacarpals for 5 seconds. Excess fluid was allowed to drain back into the container.

Hands were air dried for 3 minutes, holding them in a horizontal position. Each subject was encouraged to rotate hands to avoid the formation of droplets.

Each subject was treated out of the same batch of contamination fluid.

After drying, fingertips and thumb were rubbed for 1 minute on the base of a Petri-dish, which contained 10 mL of TSB. A separate Petri-dish for each hand (Left and Right) was used. This was the Pre-value.

Dilutions of $10^{-4}$ and $10^{-5}$ were prepared using sterile Peptone Water (PEP). Each dilution was spreaded onto pre-poured, dried TSA plates. The time between sampling and plating did not exceed 30 minutes.

Immediately after sampling for the pre-values and without re-contaminating the hands, the group performed the 'handwash' procedure in accordance with 8.5 and 8.6.

Reference Handwash Procedure

These steps were followed by Group 1 recruits on Day 1 and Group 2 recruits on Day 2.

3 mL of 60% propan-2-ol was dispensed onto the subject's hands and rubbed over for 30 seconds using the standard procedure as instructed. This was done twice to give total of 6 mL of 60% propan-2-ol over a 60 second rub.

The reference procedure was completed with a 5 second rinse of fingers under running tap water.

Test Product Procedure

These steps were followed by Group 1 on Day 2 and Group 2 on Day 1.

3 mL of test product was dispensed onto the subject's hands and rubbed over for 30 seconds using the standard procedure as instructed. This was done twice to give total of 6 mL test product over 60 second rub.

The test product procedure was completed with a 5 seconds rinse of fingers under running tap water.

Post-Values

The Post-value was obtained by rubbing the fingertips and thumb on the base of a Petri dish containing 10 mL of either T6 or PDE Broth as inactivating agent (dilution of $10^0$). Dilutions of $10^0$, $10^{-1}$ and $10^{-2}$ were spreaded on pre-poured and dried TSA plates.

All plates were incubated at 36° C.±2° C. for 24-48 hours.

Results and Calculations

After the incubation period, all the plates were checked and colony forming units on both reference and test sample were counted. Dilutions with counts that are within 15-300 cfu were used in the computation.

Plates showing less than 15 cfu or no growth were also counted.

Data were collected from 15 volunteers, but only 14 were taken into account as the results of plate count from one subject were evidently improbable and hence excluded. With 14 subjects, the test remains in compliance with the minimum requirement of 12. No other deviation to the experimental protocol was required.

Raw data and statistical evaluations are given in Table 9.1-Table 9.6 (pages 7-12).

Acceptance Criteria

In Accordance with the Criteria Specified in EN 1500:

All results from at least 12 subjects shall be available. In this study, 14 set of data are available.

The over all mean of the log prevalues for the reference and test product shall be at least 5.00. In this study, the mean was 7.13 and 7.01 respectively.

In each procedure, R and P, not more than three subjects with log reduction factor lower than 3.00. In this study, the lowest log reduction recorded was 3.94.

For any product, the mean log reduction factor obtained shall not be significantly smaller than that of the reference propan-2-ol. In this study, the mean log reduction for P is higher than that of R, with a mean difference of 0.54.

If the mean log reduction factor of a test product is smaller than that of the reference propan-2-ol, the difference shall be tested for statistical significance. In this study, the mean log reduction factor of the test product is greater than that of the reference, no further statistical analysis is deemed necessary.

Discussion

The log reduction of contaminant bacteria by 5.7 may be regarded as comparable, albiet close, having surpassed the reference preparation (5.16 logs) and according to the acceptance criteria, this is within the acceptable level of confidence Experimental Results—Reference (Propan-2-131) Solution Preparation: 60% Propan-2-ol Application: rub-in 3 mL for 30 seconds, repeat once (Total 6 mL for 1 minute) Test Organism: *Escherichia coli* (NCTC 10538)

Suspension: $1.0 \times 10^9$ cfu/mL

| Subject | | Number of cfu per Plate from Dilution 1 e | | | | | |
|---|---|---|---|---|---|---|---|
| | | Prevalues | | Postvalues | | | |
| No | Hand | $10^{-4}$ | $10^{-5}$ | $10^{-0}$ | $10^{-1}$ | $10^{-2}$ | |
| 1 | L | TNTC/TNTC | 96 | 113 | 19/22 | 0/0 | 0/0 |
| | R | TNTC/TNTC | 92 | 86 | 54/69 | 8/8 | 0/1 |
| 2 | L | TNTC/TNTC | 90 | 87 | TNTC/TNTC | 1/5 | 0/0 |
| | R | TNTC/TNTC | 80 | 72 | 86/62 | 1/11 | 0/0 |
| 3 | L | TNTC/TNTC | 152 | 170 | 3/10 | 0/0 | 0/0 |
| | R | TNTC/TNTC | 135 | 155 | 21/22 | 1/2 | 0/0 |
| 4 | L | TNTC/TNTC | 89 | 100 | TNTC/TNTC | 108/94 | 5/16 |
| | R | TNTC/TNTC | 100 | 92 | 42/41 | 9/3 | 0/3 |
| 5 | L | TNTC/TNTC | 83 | 68 | TNTC/TNTC | 177/129 | 11/19 |
| | R | TNTC/TNTC | 92 | 96 | TNTC/TNTC | 62/63 | 2/4 |
| 6 | L | TNTC/TNTC | 144 | 123 | 0/0 | 1/0 | 0/0 |
| | R | TNTC/TNTC | 117 | 112 | 5/4 | 5/3 | 0/1 |

-continued

| Subject | | Number of cfu per Plate from Dilution 1 e | | | | |
|---|---|---|---|---|---|---|
| | | Prevalues | | Postvalues | | |
| No | Hand | $10^{-4}$ | $10^{-5}$ | $10^{-0}$ | $10^{-1}$ | $10^{-2}$ |
| 7 | L | TNTC/TNTC | 93 | 76 | 0/0 | 0/0 | 0/0 |
| | R | TNTC/TNTC | 126 | 119 | 0/0 | 0/0 | 0/0 |
| 8 | L | TNTC/TNTC | 245 | 256 | TNTC/TNTC | 20/27 | 2/1 |
| | R | TNTC/TNTC | 214 | 217 | TNTC/TNTC | 50/41 | 3/9 |
| 9 | L | TNTC/TNTC | 113 | 105 | 58/46 | 0/0 | 0/0 |
| | R | TNTC/TNTC | 104 | 97 | 134/120 | 2/0 | 0/0 |
| 10 | L | TNTC/TNTC | 167 | 159 | TNTC/TNTC | 26/22 | 7/3 |
| | R | TNTC/TNTC | 133 | 135 | TNTC/TNTC | 141/142 | 11 |
| 11 | L | TNTC/TNTC | 415 | 325 | TNTC/TNTC | TNTC/TNTC | 16/ |
| | R | TNTC/TNTC | 308 | 260 | TNTC/TNTC | TNTC/TNTC | 56/ |
| 12 | L | TNTC/TNTC | 197 | 179 | 4/3 | 0/0 | 0/0 |
| | R | TNTC/TNTC | 206 | 214 | 5/5 | 0/5 | 0/0 |
| 13 | L | TNTC/TNTC | 85 | 59 | TNTC/TNTC | 18/15 | 0/2 |
| | R | TNTC/TNTC | 115 | 120 | TNTC/TNTC | 9/16 | 1/0 |
| 14 | L | TNTC/TNTC | 89 | 123 | TNTC/TNTC | 17/30 | 10/9 |
| | R | TNTC/TNTC | <u>117</u> | <u>111</u> | TNTC/TNTC | <u>62/76</u> | 17 16/ |
| 15 | L | TNTC/TNTC | 183 | 182 | 246/275 | 26/24 | 1/2 |
| | R | TNTC/TNTC | 212 | 174 | 232/182 | 19/23 | 3/5 |

Underline counts were used in the computation

Experimental Results—Test (Handrub) Solution
Preparation: Test Sample Neat
Application: rub-in 3 mL for 30 seconds, repeat once Test Organism: *Escherichia coli* (NCTC 10538)
Suspension: $1.0 \times 10^9$ cfu/mL

| Subject No | Hand | Number of cfu per Plate from Dilution $10^x$ | | | | |
|---|---|---|---|---|---|---|
| | | Prevalues | | Postvalues | | |
| | | $10^{-4}$ | $10^{-5}$ | $10^{-0}$ | $10^{-1}$ | $10^{-2}$ |
| 1 | L | TNTC/TNTC | 76 | 100 | 6/3 | 0/0 | 0/0 |
| | R | TNTC/TNTC | 69 | 77 | 0/5 | 0/0 | 0/0 |
| 2 | L | TNTC/TNTC | 52 | 58 | 4/3 | 1/1 | 0/0 |
| | R | TNTC/TNTC | 12 | 5 | 2/3 | 1/1 | 0/0 |
| 3 | L | TNTC/TNTC | 84 | 107 | 15/9 | 1/3 | 0/0 |
| | R | TNTC/TNTC | 46 | 35 | 4/1 | 0/0 | 0/0 |
| 4 | L | TNTC/TNTC | 89 | 100 | TNTC | 108/94 | 5/16 |
| | R | TNTC/TNTC | 100 | 92 | 42/41 | 9/3 | 3/0 |
| 5 | L | TNTC/TNTC | 135 | 118 | TNTC/TNTC | 54/66 | 6/5 |
| | R | TNTC/TNTC | 141 | 130 | TNTC/TNTC | 160/148 | 27/28 |
| 6 | L | TNTC/TNTC | 144 | 133 | 3/8 | 0/0 | 0/0 |
| | R | TNTC/TNTC | 160 | 174 | 55/42 | 3/0 | 0/0 |
| 7 | L | TNTC/TNTC | 120 | 88 | 10/12 | 0/0 | 0/0 |
| | R | TNTC/TNTC | 123 | 80 | 9/14 | 0/0 | 0/0 |
| 8 | L | TNTC/TNTC | 136 | 141 | TNTC/TNTC | 12/15 | 0/0 |
| | R | TNTC/TNTC | 46 | 99 | TNTC/TNTC | 20/22 | 0/1 |
| 9 | L | TNTC/TNTC | 84 | 129 | 50/44 | 0/0 | 0/0 |
| | R | TNTC/TNTC | 52 | 148 | 58/78 | 1/1 | 0/0 |
| 10 | L | TNTC/TNTC | 60 | 37 | TNTC/TNTC | 79/90 | 8/14 |
| | R | TNTC/TNTC | 28 | 36 | 59/83 | 3/8 | 0/1 |
| 11 | L | TNTC/TNTC | 517 | 496 | TNTC | 1/4 | 0/0 |
| | R | TNTC/TNTC | 405 | 419 | TNTC | 7/4 | 1/0 |
| 12 | L | TNTC/TNTC | 159 | 147 | 1/1 | 0/2 | 0/1 |
| | R | TNTC/TNTC | 238 | 245 | 0/0 | 0/1 | 0/0 |
| 13 | L | TNTC/TNTC | 46 | 67 | 14/8 | 0/1 | 1/1 |
| | R | TNTC/TNTC | 98 | 89 | 1/0 | 1/0 | 1/1 |
| 14 | L | TNTC/TNTC | 154 | 180 | 35/73 | 0/2 | 2/0 |
| | R | TNTC/TNTC | 127 | 114 | 45/61 | 4/4 | 0/0 |
| 15 | L | TNTC/TNTC | 243 | 212 | 1/2 | 0/0 | 0/0 |
| | R | TNTC/TNTC | 146 | 147 | 8/9 | 1/0 | 0/0 |

Underline counts were used in the computation

| List of Log Values (Mean of Left & Right Hand) - Reference Wash | | | | | | | |
|---|---|---|---|---|---|---|---|
| Subject No | | Prevalues | Log X | Ave. Log X | Postvalues | Log Y | Ave. Log Y |
| 1 | L | 10450000 | 7.02 | 6.98 | 21 | 1.32 | 1.55 |
|   | R | 8900000 | 6.95 |   | 61 | 1.79 |   |
| 2 | L | 8850000 | 6.95 | 6.91 | 30 | 1.48 | 1.67 |
|   | R | 7600000 | 6.88 |   | 74 | 1.87 |   |
| 3 | L | 16100000 | 7.21 | 7.18 | 7 | 0.85 | 1.09 |
|   | R | 14500000 | 7.16 |   | 22 | 1.34 |   |
| 4 | L | 7550000 | 6.88 | 6.93 | 1530 | 3.18 | 2.99 |
|   | R | 9400000 | 6.97 |   | 625 | 2.80 |   |
| 5 | L | 13350000 | 7.13 | 7.09 | 5 | 0.70 | 0.70 |
|   | R | 11450000 | 7.06 |   | 5 | 0.70 |   |
| 6 | L | 8450000 | 6.93 | 7.01 | 0 | 1.00 | 1.00 |
|   | R | 12250000 | 7.09 |   | 0 | 1.00 |   |
| 7 | L | 25050000 | 7.40 | 7.37 | 235 | 2.37 | 2.51 |
|   | R | 21550000 | 7.33 |   | 455 | 2.66 |   |
| 8 | L | 10900000 | 7.04 | 7.02 | 52 | 1.72 | 1.91 |
|   | R | 10050000 | 7.00 |   | 127 | 2.10 |   |
| 9 | L | 16300000 | 7.21 | 7.17 | 240 | 2.38 | 2.77 |
|   | R | 13400000 | 7.13 |   | 1415 | 3.15 |   |
| 10 | L | 37000000 | 7.57 | 7.51 | 2050 | 3.31 | 3.54 |
|   | R | 28400000 | 7.45 |   | 5950 | 3.77 |   |
| 11 | L | 18800000 | 7.27 | 7.30 | 4 | 0.60 | 0.65 |
|   | R | 21000000 | 7.32 |   | 5 | 0.70 |   |
| 12 | L | 7200000 | 6.86 | 6.96 | 165 | 2.22 | 2.16 |
|   | R | 11750000 | 7.07 |   | 125 | 2.10 |   |
| 13 | L | 10600000 | 7.03 | 7.04 | 235 | 2.37 | 2.60 |
|   | R | 11400000 | 7.06 |   | 690 | 2.84 |   |
| 14 | L | 18250000 | 7.26 | 7.27 | 250 | 2.40 | 2.36 |
|   | R | 19300000 | 7.29 |   | 210 | 2.32 |   |
| Average |   |   |   | 7.13 |   |   | 1.97 |
| SD |   |   |   | 0.18 |   |   | 0.89 |
| N |   |   |   | 14.00 |   |   | 14 |

N = Number of Subjects

| List of Log Values (Mean of Left & Right Hand) - Sunnywipes (Test Sample) | | | | | | | |
|---|---|---|---|---|---|---|---|
| Subject No | | Prevalues | Log X | Ave. Log X | Postvalues | Log Y | Ave. Log Y |
| 1 | L | 8800000 | 6.94 | 6.90 | 5 | 0.70 | 0.59 |
|   | R | 7300000 | 6.86 |   | 3 | 0.48 |   |
| 2 | L | 5500000 | 6.74 | 6.33 | 4 | 0.60 | 0.54 |
|   | R | 850000 | 5.93 |   | 3 | 0.48 |   |
| 3 | L | 9550000 | 6.98 | 6.79 | 12 | 1.08 | 0.78 |
|   | R | 4050000 | 6.61 |   | 3 | 0.48 |   |
| 4 | L | 12650000 | 7.10 | 7.12 | 600 | 2.78 | 3.00 |
|   | R | 13550000 | 7.13 |   | 1650 | 3.22 |   |
| 5 | L | 13850000 | 7.14 | 7.18 | 6 | 0.78 | 1.23 |
|   | R | 16700000 | 7.22 |   | 49 | 1.69 |   |
| 6 | L | 10400000 | 7.02 | 7.01 | 11 | 1.04 | 1.06 |
|   | R | 10150000 | 7.01 |   | 12 | 1.08 |   |
| 7 | L | 13850000 | 7.14 | 7.00 | 135 | 2.13 | 2.23 |
|   | R | 7250000 | 6.86 |   | 210 | 2.32 |   |
| 8 | L | 10650000 | 7.03 | 7.01 | 47 | 1.67 | 1.75 |
|   | R | 10000000 | 7.00 |   | 68 | 1.83 |   |
| 9 | L | 4850000 | 6.69 | 6.60 | 845 | 2.93 | 2.39 |
|   | R | 3200000 | 6.51 |   | 71 | 1.85 |   |
| 10 | L | 50650000 | 7.70 | 7.66 | 3 | 0.48 | 1.11 |
|   | R | 41200000 | 7.61 |   | 55 | 1.74 |   |
| 11 | L | 15300000 | 7.18 | 7.28 | 1 | 0.00 | 0.35 |
|   | R | 24150000 | 7.38 |   | 5 | 0.70 |   |
| 12 | L | 5650000 | 6.75 | 6.86 | 11 | 1.04 | 0.87 |
|   | R | 9350000 | 6.97 |   | 5 | 0.70 |   |
| 13 | L | 16700000 | 7.22 | 7.15 | 54 | 1.73 | 1.73 |
|   | R | 12050000 | 7.08 |   | 53 | 1.72 |   |
| 14 | L | 22750000 | 7.36 | 7.26 | 3 | 0.48 | 0.72 |
|   | R | 14650000 | 7.17 |   | 9 | 0.95 |   |
| Average |   |   |   | 7.01 |   |   | 1.31 |
| SD |   |   |   | 0.32 |   |   | 0.79 |
| N |   |   |   | 14.00 |   |   | 14 |

N = Number of Subjects

| Log Reduction Derived from Reference and Test Sample | | | | | |
| --- | --- | --- | --- | --- | --- |
| Reference (R) Propan-2-ol 60% (v/v) | | | Test Product (P) Sunnywipe Handwash | | |
| Subject | Log X | Log Y | Log Z | Log X | Log Y | Log Z |

| Subject | Log X | Log Y | Log Z | Log X | Log Y | Log Z |
| --- | --- | --- | --- | --- | --- | --- |
| 1 | 6.98 | 1.55 | 5.43 | 6.90 | 0.59 | 6.32 |
| 2 | 6.91 | 1.67 | 5.24 | 6.33 | 0.54 | 5.80 |
| 3 | 7.18 | 1.09 | 6.09 | 6.79 | 0.78 | 6.02 |
| 4 | 6.93 | 2.99 | 3.94 | 7.12 | 3.00 | 4.12 |
| 5 | 7.09 | 0.70 | 6.39 | 7.18 | 1.23 | 5.95 |
| 6 | 7.01 | 1.00 | 6.01 | 7.01 | 1.06 | 5.95 |
| 7 | 7.37 | 2.51 | 4.85 | 7.00 | 2.23 | 4.77 |
| 8 | 7.02 | 1.91 | 5.11 | 7.01 | 1.75 | 5.26 |
| 9 | 7.17 | 2.77 | 4.40 | 6.60 | 2.39 | 4.21 |
| 10 | 7.51 | 3.54 | 3.97 | 7.66 | 1.11 | 6.55 |
| 11 | 7.30 | 0.65 | 6.65 | 7.28 | 0.35 | 6.93 |
| 12 | 6.96 | 2.16 | 4.81 | 6.86 | 0.87 | 5.99 |
| 13 | 7.04 | 2.60 | 4.44 | 7.15 | 1.73 | 5.42 |
| 14 | 7.27 | 2.36 | 4.91 | 7.26 | 0.72 | 6.55 |
| Mean | 7.13 | 1.97 | 5.16 | 7.01 | 1.31 | 5.70 |
| SD | 0.18 | 0.89 | 0.86 | 0.32 | 0.79 | 0.86 |

Example 6—Bacterial Disinfection Test

Objective

To determine whether the formulation of Example 1 demonstrated bactericidal activity required to meet the Australian Therapeutic Goods Administration (TGA) disinfection test, option D against six significant infective bacteria. The test followed the protocol of method TM122-04.

Conditions

Test organisms: 1. *Staphylococcus aureus* NCTC 4163

2. *Escherichia coli* NCTC 8196

3. *Pseudomonas aeruginosa* NCTC 6749

4. *Proteus vulgaris* NCTC 4635

5. Methicillin Resistant *Staphylococcus aureus* (MRSA)

6. Vancomycin Resistant Enterobacteria (VRE)

Inoculum Level Approx. 1.7 to $3.6 \times 10^6$ Colony Forming Units (CFU)/mL

Test Concentration Neat

Contact Times: 30 seconds

Test Temperature Ambient

Results

No growth of any of the bacterial organisms tested for was identified after exposure to the test formulation, which the control inoculations behaved as expected. The test formulation successfully demonstrated bactericidal activity according to the TGA disinfection test, option D standard.

Example 7—Anti-Microbial Activity Challenge Test (TM110)

Objective

To determine whether the formulation of Example 1 demonstrated anti-microbial activity against Methicillin-resistant *Staphylococcus aureus* and Vancomycin-resistant *Enterococcus faecalis*.

Conditions

Test organisms: 1. Methicillin-resistant *Staphylococcus aureus* (MRSA)

2. Vancomycin-resistant *Enterococcus faecalis* (VRE)

Test Concentration Neat

Contact Times: 30 seconds and 2 minutes

Test Temperature: Ambient

Results

TABLE 2

Surviving MRSA after exposure to test formulation

| | Surviving organisms (CFU/mL) and $Log_{10}$ Reduction | | | |
| --- | --- | --- | --- | --- |
| | 30 sec | | 2 minute | |
| Sample Details | CFU/mL ($log_{10}$) | Log Reduction | CFU/mL (login) | Log Reduction |
| SunnyWipes Handrub | <10 (<1) | >4.72 | <10 (<1) | >4.72 |
| Inoculum | | $5.3 \times 10^5$ (5.72 Logs) | | |

CFU = Colony Forming Unit

TABLE 3

Surviving VRE after exposure to test formulation

| | Surviving organisms (CFU/mL) and $Log_{10}$ Reduction | | | |
| --- | --- | --- | --- | --- |
| | 30 sec | | 2 minute | |
| Sample Details | CFU/mL ($log_{10}$) | Log Reduction | CFU/mL ($log_{10}$) | Log Reduction |
| SunnyWipes Gel | <10 (<1) | >4.61 | <10 (<1) | >4.61 |
| Inoculum | | $4.1 \times 10^5$ (5.61 Logs) | | |

CFU = Colony Forming Unit

Conclusions

The test formulation successfully demonstrated anti-microbial activity against Methicillin-resistant *Staphylococcus aureus* and Vancomycin-resistant *Enterococcus faecalis* by more than 4 log reduction (kill >99.99%) after 30 seconds and 2 minutes of contact time, when tested neat in conditions described above.

Example 7a—Antimicrobial Activity Challenge Test (TM 110-04)

Objective

To determine whether the formula of Example 2 demonstrates anti-microbial activity against *pseudomonas aeruginosa*, inter alia.

Conditions:

Test Organisms: *pseudomonas aeruginosa* ATCC 15442

Neutraliser: T6 1:100 (TSB with Lecithin and Tween 80)

Test Concentration: Neat

Contact Time: 15 and 30 seconds

Test Temperature Ambient

Results:

Surviving Organisms after 15 and 30 seconds exposure to Antimicrobial Hand Rub

*Pseudomonas aeruginosa*

| Contact Time | CFU/mL ($\log_{10}$) | Log Reduction |
|---|---|---|
| 15 seconds | <100 (2.00) | >5.70 |
| 30 seconds | <100 (2.00) | >5.70 |
| Inoculum count | $5.0 \times 10^7$ (7.70) | |

Comments:

The sample Example 2 has demonstrated bactericidal activity against *Pseudomonas aeruginosa* by showing greater than 5 Log reduction which equates to 99.999% kill at 15 and 30 seconds contact time when tested under the conditions described above.

EXAMINATION: TGA (Australian Therapeutic Goods Administration) Disinfectant Test, Option D DILUTION: Neat

METHOD: TM122-04

NEUTRALISER: T6

Results:

| Test Date | Organisms | Sub-culture No. | Inoculum (CFU/mL) | Challenge Result | Controls |
|---|---|---|---|---|---|
| 16, May 2012 | Staphylococcus aureus | 5 | $1.1 \times 10^6$ | — | C1- |
| | Escherichia coli | 5 | $2.3 \times 10^6$ | — | C2- |
| | Pseudomonas aeruginosa | 5 | $2.1 \times 10^6$ | — | C3+++ +++ |
| | Proteus vulgaris | 5 | $2.0 \times 10^6$ | — | |
| | Methicillin Resistant Staphylococcus aureus | 5 | $2.9 \times 10^6$ | — | C4+++ +++ |
| | Vancomycin Resistant Enterococcus faecalis | 5 | $1.6 \times 10^6$ | — | |
| 17, May 2012 | Staphylococcus aureus | 6 | $1.9 \times 10^6$ | — | C1- |
| | Escherichia coli | 6 | $2.3 \times 10^6$ | — | C2- |
| | Pseudomonas aeruginosa | 6 | $2.1 \times 10^6$ | — | C3+++ +++ |
| | Proteus vulgaris | 6 | $2.1 \times 10^6$ | — | |
| | Methicillin Resistant Staphylococcus aureus | 6 | $2.4 \times 10^6$ | — | C4+++ +++ |
| | Vancomycin Resistant Enterococcus faecalis | 6 | $1.6 \times 10^6$ | — | |
| 18, May 2012 | Staphylococcus aureus | 7 | $1.7 \times 10^6$ | — | C1- |
| | Escherichia coli | 7 | $1.7 \times 10^6$ | — | C2- |
| | Pseudomonas aeruginosa | 7 | $2.1 \times 10^6$ | — | C3+++ +++ |
| | Proteus vulgaris | 7 | $2.4 \times 10^6$ | — | |
| | Methicillin Resistant Staphylococcus aureus | 7 | $2.3 \times 10^6$ | — | C4+++ +++ |
| | Vancomycin Resistant Enterococcus faecalis | 7 | $2.0 \times 10^6$ | — | |

Where

"-" Denotes No Growth

"+" Denotes Growth

"C1" Denotes media sterility check. Must be negative for a valid result

"C2" Denotes sample sterility check. Must be negative for a valid result

"C3" Denotes organism viability check. Must be positive for a valid result

"C4" Denotes neutralizer toxicity check. Must be positive for a valid result

Final Results:

The sample Example 2 passed the TGA Disinfectant Test, Option D when tested under the conditions described above.

Notes:

1. Strains of Organisms used were as follows

| Organism | AMS Culture No. | NCTC No. |
|---|---|---|
| Staphylococcus aureus | AMS 028 | NCTC 4163 |
| Escherichia coli | AMS 007 | NCTC 8196 |
| Pseudomonas aeruginosa | AMS 018 | NCTC 6749 |
| Proteus vulgaris | AMS 016 | NCTC 4635 |
| Methicillin Resistant Staphylococcus aureus | AMS 077 | NA |
| Vancomycin Resistant Enterococcus faecalis | AMS 084 | NA |

2. Results of controls confirm to expected outcome

Example 8—Evaluation of Trans-Epidermal Water Loss

Objective

The effect of the formulation of Example 1 on skin hydration was evaluated using a TEWA Meter and compared with untreated skin on the same test subjects at 30 min, 2 days and 6 days.

Standards for Inclusion in a Study

1. Individuals between the ages of 18 and 70.
2. Individuals not taking medication or under the care of a physician for a period of one month prior to commencement and throughout the entire test period.
3. Individuals who have completed a preliminary medical history questionnaire.
4. Individuals who have read, understood and signed an informed consent document.
5. Individuals who understand the instructions for use and are willing to cooperate with the program as stated.
6. Individuals free of any dermatological or systemic disorder that would interfere with the results, at the discretion of the Investigator.
7. Individuals able to cooperate with the Investigator and the research staff and willing to complete the full course of the study.

Standards for Exclusion from a Study

1. Individuals who are under doctors' care.
2. Individuals who are currently taking medication which in the opinion of the Investigator would mask or interfere with the results.

3. Individuals with any history of sensitivity to cosmetics in general and moisturisers in particular.
4. Individuals with any form of skin cancer, melanoma, lupus, psoriasis, rosacea, porphyria cutanea tarda, connective tissue disease, or any disease that would interfere with the test results.
5. Individuals diagnosed with chronic skin allergies.
6. Female volunteers who indicate that they are pregnant or nursing an infant.
7. Individuals with excessive hair on the test sites.
8. Individuals with known hypersensitivity to cosmetic products.

Informed Consent

A signed informed consent was obtained from each panelist prior to initiating the study describing reasons for the study, possible adverse effects, associated risks and potential benefits of the treatment and their limits of liability.

Methodology

One distinct method was employed for the evaluation procedure. Biophysical measurements were made pre-application (t=0) and following a single application of the test material after 30 min. Additional readings were also taken at 2 days and 6 days. Before each set of measurements, subjects were required to equilibrate in a closed environment with constant temperature (20° C.+/−2° C.) and humidity (45% to 55% RH). Measurements are expressed as g/hm².

Moisture Measurement

Model TM 210 TEWA Meter–Courage+Khazala

REFERENCES

Tewameter TM 210 Information and Operating Instructions (manual).
Transepidermal Water Loss, Bioengineering of the Skin: Methods and Instrumentation, CRC Press 1995.
Dermatest SOP DESOP—030 Procedure for Determining Transepidermal Water Loss (TEWL).

Study Design 11 healthy subjects between the ages of 33 to 58 years were inducted into this study. In order to precondition the test sites and keep all topical treatments constant for all test subjects they were required to abstain from using deodorant soaps, moisturising soaps or cosmetic moisturisers on the test area for a period of one week prior to study commencement and during the course of the study. At the completion of the one week 'washout' period, subjects were required to return to the test facility at the time specified by the technician for the study commencement. On the day of the study, test material was delivered to the test sites by applying to the back of the hands liberally. Subjects were blinded as to the nature of the material being applied. Biophysical measurements with a TEWA Meter were taken at t=0 (pre-application). Subjects were required to return to the lab at each subsequent designated period for repeat biophysical measurements.

Results

TABLE 4

| Trans-epidermal water loss | | | |
|---|---|---|---|
| t = 0 | t = 30 min | t = 2 days | t = 6 days |
| 11.13 | 7.48 | 6.15 | 4.77 |
| % diff | −32.8% | −44.8% | −57.1% |

Conclusions

After repeat applications over a period of 6 days, the formulation was shown to have a positive impact as transepidermal water loss was significantly reduced. There was no incidence of skin irritation under the test conditions.

Example 9—Skin Irritation Testing 1.0 Objective

Consumer products or raw materials designed for consistent reapplication to areas of the skin may, under proper conditions, prove to be contact sensitizers or irritants in certain individuals. It is the intention of a Repeat Insult Patch Test (RIPT) to provide a basis for evaluation of this irritation/sensitization potential if such exists.

2.0 Reference

The method is modified to test 50 panelists and not the 200 cited in the reference *Appraisal of the Safety of Chemicals in Food, Drugs and Cosmetics*, published by the Association of Food and Drug Officials of The United States. The method also employs nine inductive patchings and not the ten cited in the reference under semi-occlusive patch conditions.

3.0 Test Material:

Formulation produced according to Example 1.

4.0 Panel Selection.

4.1 Standards for Inclusion in a Study

Individuals who are not currently under a doctor's care.
Individuals free of any dermatological or systemic disorder which would interfere with the results, at the discretion of the Investigator.
Individuals free of any acute or chronic disease that might interfere with or increase the risk of study participation.
Individuals who will complete a preliminary medical history form and are in general good health.
Individuals who will read, understand and sign an informed consent document relating to the specific type of study they are subscribing.
Individuals able to cooperate with the Investigator and research staff, willing to have test materials applied according to the protocol, and complete the full course of the study.

4.2 Standards for Exclusion from a Study

Individuals under 18 years of age.
Individuals who are under doctor's care.
Individuals who are currently taking any medication (topical or systemic) that may mask or interfere with the test results.
Subjects with a history of any acute or chronic disease that might interfere with or increase the risk of study participation.
Individuals diagnosed with chronic skin allergies.
Female volunteers who indicate that they are pregnant or nursing.

4.3 Recruitment

Panel selection is accomplished by advertisement in local periodicals, community bulletin boards, phone solicitation, electronic media or any combination thereof.

4.4 Informed Consent and Medical History Forms

An informed consent was obtained from each volunteer prior to initiating the study describing reasons for the study, possible adverse effects, associated risks and potential benefits of the treatment and their limits of liability. Panelists signed and dated the informed consent document to indicate their authorization to proceed and acknowledge their understanding of the contents. Each subject was assigned a permanent identification number and completed an extensive medical history form.

5.0 Population Demographics

| Number of subjects enrolled | | 54 |
|---|---|---|
| Number of subjects completing study | | 53 |
| Age Range | | 21-67 |
| Sex | Male | 14 |
| | Female | 40 |
| Race | Caucasian | 19 |
| | Hispanic | 1 |
| | Asian | 5 |
| | African American | 29 |

6.0 Equipment
- Patch Description: Parke-Davis Hypoallergenic Readi Bandages (20×20 mm Webril affixed to the centre of a 40×40 mm adhesive bandage) or the equivalent, trimmed at right angles on opposite sides to the opening of the paper backing of patch, allowing air flow.
- 1 ml volumetric syringe without a needle.

7.0 Procedure
- Subjects are requested to bathe or wash as usual before arrival at the facility.
- 0.2 ml of the test material was dispensed onto a semi-occlusive, hypoallergenic patch.
- The patch was then affixed directly to the skin of the infrascapular regions of the back, to the right or left of the midline and the subject was dismissed with instructions not to wet or expose the test area to direct sunlight.
- After 24 hours the patch was removed by the panelist at home.
- This procedure was repeated until a series of nine consecutive 24 hour exposures have been made for every Monday, Wednesday and Friday for three consecutive weeks.
- In the event of an adverse reaction, the area of erythema and edema is measured. The edema is estimated by the evaluation of the skin with respect to the contour of the unaffected normal skin. Reactions are scored just before applications two through nine and the next test date following application nine. Clients are notified immediately in the case of adverse reaction and determination is made as to treatment program if necessary.
- Subjects were then given a 10-14 day rest period after which a challenge or retest dose was applied once to a previously unexposed test site. The retest dose is equivalent to any one of the original nine exposures. Reactions are scored 24 and 48 hours after application. Comparison was made between the nine sensitizing doses and the retest dose.
- At the end of the study, the consulting Dermatologist revised this data and confirmed the stated conclusions.

8.0 Results

No adverse reactions of any kind were noted during the course of this study.

10. Conclusions

The test material when tested under semi-occlusive conditions as described herein, can be considered as a non-primary irritant and a non-primary sensitizer to the skin according to the reference.

Example 10—Surface Persistence Test

Objective

To determine whether terpinen-4-ol from the formulation of Example 1 will persist on a surface for a period of time after application Method The test surface was a smooth melamine laboratory bench top. The surface was prepared by cleaning with 100% EtOH and allowing to dry. The test formulation (one pump from a plastic hand pump (+/−2 g)) was evenly spread over the estimated surface area of a human hand (400 cm$^2$) using a rubber finger cot. Duplicate sample areas were prepared. Samples were taken after 3 hours and 6 hours with a cotton swab by wiping the whole area with 20 swipes of the swab. The swab samples were placed in test tubes containing 5 mL (10% methanol in acetone) and analyzed through gas chromatography (GC) using the validated method MTCS-220.

Results

Analyte tested for—Terpinen-4-ol
- 3 Hours—Area A Present
- 3 Hours—Area B Present
- 6 Hours—Area A None Detected
- 6 Hours—Area B None Detected Standard Check Terpinen-4-ol (0.45 mg/mL) 98.0%

These results demonstrate persistence of terpinen-4-ol on a surface at least 3 hours following application.

Example 11—Skin Hydration Test

Objective

The effect of the formulation of Example 1 on skin hydration was evaluated using a Corneometer, compared with untreated skin on the same test subjects at 30 min, 2 days and 6 days.

Standards for Inclusion in a Study
1. Individuals between the ages of 25 and 65.
2. Individuals not taking medication or under the care of a physician for a period of one month prior to commencement and throughout the entire test period.
3. Individuals who have completed a preliminary medical history questionnaire.
4. Individuals who have read, understood and signed an informed consent document.
5. Individuals who understand the instructions for use and are willing to cooperate with the program as stated.
6. Individuals free of any dermatological or systemic disorder that would interfere with the results, at the discretion of the Investigator.
7. Individuals able to cooperate with the Investigator and the research staff and willing to complete the full course of the study.

Standards for Exclusion from a Study
1. Individuals who are under doctors' care.
2. Individuals who are currently taking medication which in the opinion of the Investigator would mask or interfere with the results.
3. Individuals with any history of sensitivity to cosmetics in general and moisturisers in particular.
4. Individuals with any form of skin cancer, melanoma, lupus, psoriasis, rosacea, porphyria cutanea tarda, connective tissue disease, or any disease that would interfere with the test results.
5. Individuals diagnosed with chronic skin allergies.
6. Female volunteers who indicate that they are pregnant or nursing an infant.
7. Individuals with excessive hair on the test sites.
8. Individuals with known hypersensitivity to cosmetic products.

Informed Consent

A signed informed consent was obtained from each panelist prior to initiating the study describing reasons for the study, possible adverse effects, associated risks and potential benefits of the treatment and their limits of liability.

Methodology

One distinct method was employed for the evaluation procedure. Biophysical measurements were made pre-application (t=0) and following a single application of the test material after 30 min. Additional readings were also taken at 2 days and 6 days. Before each set of measurements, subjects were required to equilibrate in a closed environment with constant temperature (20° C.+/−2° C.) and humidity (45% to 55% RH).

Moisture Measurement—Corneometer

Model CM 825 PC Corneometer–Courage+Khazala

Study Design 5 healthy subjects between the ages of 33 to 58 years were inducted into this study. In order to precondition the test sites and keep all topical treatments constant for all test subjects they were required to abstain from using deodorant soaps, moisturising soaps or cosmetic moisturisers on the test area for a period of one week prior to study commencement and during the course of the study. At the completion of the one week 'washout' period, subjects were required to return to the test facility at the time specified by the technician for the study commencement.

On the day of the study, test material was delivered to the test sites by applying to the back of the hands liberally. Subjects were blinded as to the nature of the material being applied. Biophysical measurements with a Corneometer were taken at t=0 (pre-application). Subjects were required to return to the lab at each subsequent designated period for repeat biophysical measurements.

Results

TABLE 5

| Skin hydration | | | |
|---|---|---|---|
| t = 0 | t = 30 min | t = 2 days | t = 6 days |
| 26.4 | 33.7 | 43.0 | 46.2 |
| % diff | 27.7% | 63.0% | 74.8% |

Conclusions

After repeat applications over a period of 6 days, the formulation was shown to provide effective moisturisation under the conditions of the test. There was no incidence of skin irritation under the test conditions.

Example 12

EXAMINATION: Anti-microbial Activity Challenge Test (Time-Kill Study)

METHOD: TMF 110-04

Conditions:

Test organisms: *Pseudomonas aeruginosa* ATCC 15442

Neutraliser: T6 1:100 (TSB with Lecithin and Tween 80)

Test Concentration: Neat

Contact Time: 15 and 30 seconds

Test Temperature Ambient

Results:

TABLE 1

| | Surviving Organisms after 15 and 30 seconds exposure to Antimicrobial Hand Gel | |
|---|---|---|
| | *Pseudomonas aeruginosa* | |
| Contact Time | CFU/mL ($\log_{10}$) | Log Reduction |
| 15 seconds | <100 (2.00) | >5.70 |
| 30 seconds | <100 (2.00) | >5.70 |
| Inoculum count | $5.0 \times 10^7$ (7.70) | |

Comments:

The sample Example 3 (Hand Gel) has demonstrated bactericidal activity against *Pseudomonas aeruginosa* by showing greater than 5 Log reduction which equates to 99.999% kill at 15 and 30 seconds contact time when tested under the conditions described above.

EXAMINATION: TGA (Australian Therapeutic Goods Administration) Disinfectant Test, Option D DILUTION: Neat

METHOD: TM122-04

NEUTRALISER: T6

Results:

| Test Date | Organisms | Sub-culture No. | Inoculum (CFU/mL) | Challenge Result | Controls |
|---|---|---|---|---|---|
| 16, May 2012 | *Staphylococcus aureus* | 5 | $1.1 \times 10^6$ | — | C1− |
| | *Escherichia coli* | 5 | $2.3 \times 10^6$ | — | C2− |
| | *Pseudomonas aeruginosa* | 5 | $2.1 \times 10^6$ | — | C3+++ +++ |
| | *Proteus vulgaris* | 5 | $2.0 \times 10^6$ | — | +++ |
| | Methicillin Resistant *Staphylococcus aureus* | 5 | $2.9 \times 10^6$ | — | C4+++ +++ |
| | Vancomycin Resistant *Enterococcus faecalis* | 5 | $1.6 \times 10^6$ | — | |
| 17, May 2012 | *Staphylococcus aureus* | 6 | $1.9 \times 10^6$ | — | C1− |
| | *Escherichia coli* | 6 | $2.3 \times 10^6$ | — | C2− |
| | *Pseudomonas aeruginosa* | 6 | $2.1 \times 10^6$ | — | C3+++ +++ |
| | *Proteus vulgaris* | 6 | $2.1 \times 10^6$ | — | |
| | Methicillin Resistant *Staphylococcus aureus* | 6 | $2.4 \times 10^6$ | — | C4+++ +++ |
| | Vancomycin Resistant *Enterococcus faecalis* | 6 | $1.6 \times 10^6$ | — | |

-continued

| Test Date | Organisms | Sub-culture No. | Inoculum (CFU/mL) | Challenge Result | Controls |
|---|---|---|---|---|---|
| 18, May 2012 | Staphylococcus aureus | 7 | $1.7 \times 10^6$ | — | C1− |
| | Escherichia coli | 7 | $1.7 \times 10^6$ | — | C2− |
| | Pseudomonas aeruginosa | 7 | $2.1 \times 10^6$ | — | C3+++ +++ |
| | Proteus vulgaris | 7 | $2.4 \times 10^6$ | — | |
| | Methicillin Resistant Staphylococcus aureus | 7 | $2.3 \times 10^6$ | — | C4+++ +++ |
| | Vancomycin Resistant Enterococcus faecalis | 7 | $2.0 \times 10^6$ | — | |

REF NO: 1206546 -Contd.
Where
"−" Denotes No Growth
"+" Denotes Growth
"C1" Denotes media sterility check. Must be negative for a valid result
"C2" Denotes sample sterility check. Must be negative for a valid result
"C3" Denotes organism viability check. Must be positive for a valid result "C4" Denotes neutralizer toxicity check. Must be positive for a valid result Final Results:

The sample Example 3 (Hand Gel) passed the TGA Disinfectant Test, Option D when tested under the conditions described above.

Notes:

1. Strains of Organisms used were as follows

| Organism | AMS Culture No. | NCTC No. |
|---|---|---|
| Staphylococcus aureus | AMS 028 | NCTC 4163 |
| Escherichia coli | AMS 007 | NCTC 8196 |
| Pseudomonas aeruginosa | AMS 018 | NCTC 6749 |
| Proteus vulgaris | AMS 016 | NCTC 4635 |
| Methicillin Resistant Staphylococcus aureus | AMS 077 | NA |
| Vancomycin Resistant Enterococcus faecalis | AMS 084 | NA |

2. Results of controls confirm to expected outcome

Example 13

EXAMINATION: Anti-microbial Activity Challenge Test (Time-Kill Study)
METHOD: TMF 110-04
Conditions:
  Test organisms: *Pseudomonas aeruginosa* ATCC 15442
  Neutraliser: T6 1:100 (TSB with Lecithin and Tween 80)
  Test Concentration Neat
  Contact Time: 15 and 30 seconds
  Test Temperature Ambient Results:

TABLE 1

Surviving Organisms after 15 and 30 seconds exposure to Antimicrobial Hand Gel

| | Pseudomonas aeruginosa | |
|---|---|---|
| Contact Time | CFU/mL ($\log_{10}$) | Log Reduction |
| 15 seconds | <100 (2.00) | >5.70 |
| 30 seconds | <100 (2.00) | >5.70 |
| Inoculum count | $5.0 \times 10^7$ (7.70) | |

Comments:

The sample Example 2 (Hand Rub) has demonstrated bactericidal activity against *Pseudomonas aeruginosa* by showing greater than 5 Log reduction which equates to 99.999% kill at 15 and 30 seconds contact time when tested under the conditions described above.

EXAMINATION: TGA (Australian Therapeutic Goods Administration) Disinfectant Test, Option D
DILUTION: Neat
METHOD: TM122-04
NEUTRALISER: T6
Results:

| Test Date | Organisms | Sub-culture No. | Inoculum (CFU/mL) | Challenge Result | Controls |
|---|---|---|---|---|---|
| 16, May 2012 | Staphylococcus aureus | 5 | $1.1 \times 10^6$ | — | C1− |
| | Escherichia coli | 5 | $2.3 \times 10^6$ | — | C2− |
| | Pseudomonas aeruginosa | 5 | $2.1 \times 10^6$ | — | C3+++ +++ |
| | Proteus vulgaris | 5 | $2.0 \times 10^6$ | — | +++ |
| | Methicillin Resistant Staphylococcus aureus | 5 | $2.9 \times 10^6$ | — | C4+++ +++ |
| | Vancomycin Resistant Enterococcus faecalis | 5 | $1.6 \times 10^6$ | — | |
| 17, May 2012 | Staphylococcus aureus | 6 | $1.9 \times 10^6$ | — | C1− |
| | Escherichia coli | 6 | $2.3 \times 10^6$ | — | C2− |
| | Pseudomonas aeruginosa | 6 | $2.1 \times 10^6$ | — | C3+++ +++ |
| | Proteus vulgaris | 6 | $2.1 \times 10^6$ | — | |
| | Methicillin Resistant Staphylococcus aureus | 6 | $2.4 \times 10^6$ | — | C4+++ +++ |
| | Vancomycin Resistant Enterococcus faecalis | 6 | $1.6 \times 10^6$ | — | |

-continued

| Test Date | Organisms | Sub-culture No. | Inoculum (CFU/mL) | Challenge Result | Controls |
|---|---|---|---|---|---|
| 18, May 2012 | Staphylococcus aureus | 7 | $1.7 \times 10^6$ | — | C1- |
| | Escherichia coli | 7 | $1.7 \times 10^6$ | — | C2- |
| | Pseudomonas aeruginosa | 7 | $2.1 \times 10^6$ | — | C3+++ +++ |
| | Proteus vulgaris | 7 | $2.4 \times 10^6$ | — | |
| | Methicillin Resistant Staphylococcus aureus | 7 | $2.3 \times 10^6$ | — | C4+++ +++ |
| | Vancomycin Resistant Enterococcus faecalis | 7 | $2.0 \times 10^6$ | — | |

REF NO: 1206548-Contd.
Where
"−" Denotes No Growth
"+" Denotes Growth
"C1" Denotes media sterility check. Must be negative for a valid result
"C2" Denotes sample sterility check. Must be negative for a valid result
"C3" Denotes organism viability check. Must be positive for a valid result
"C4" Denotes neutralizer toxicity check. Must be positive for a valid result Final Results:

The sample Example 2 (Hand Rub) passed the TGA Disinfectant Test, Option D when tested under the conditions described above.

Notes:

1. Strains of Organisms used were as follows

| Organism | AMS Culture No. | NCTC No. |
|---|---|---|
| Staphylococcus aureus | AMS 028 | NCTC 4163 |
| Escherichia coli | AMS 007 | NCTC 8196 |
| Pseudomonas aeruginosa | AMS 018 | NCTC 6749 |
| Proteus vulgaris | AMS 016 | NCTC 4635 |
| Methicillin Resistant Staphylococcus aureus | AMS 077 | NA |
| Vancomycin Resistant Enterococcus faecalis | AMS 084 | NA |

2. Results of controls confirm to expected outcome

It will be appreciated that the present invention has been described by way of example only and that modifications and additions may be made thereto without departing from the scope of the invention as defined in the appended claims.

The claims defining the invention are as follows:

1. A disinfecting formulation for topical application to human or animal skin consisting of, by volume:
   (a) from about 60% to about 80% ethanol;
   (b) from about 5% to about 15% eucalyptus oil;
   (c) from about 2% to about 10% glycerine;
   (d) from about 0.01% to about 0.1% piroctone olamine; and
   (e) water.

2. A disinfecting formulation for topical application to human or animal skin consisting essentially of, by volume:
   (a) from about 60% to about 80% ethanol;
   (b) from about 5% to about 15% eucalyptus oil;
   (c) from about 2% to about 10% glycerine;
   (d) from about 0.01% to about 0.1% piroctone olamine; and
   (e) water.

3. A formulation according to claim 2 wherein the pH of the formulation is in the range of 6-8.5.

4. A formulation according to claim 2, in the form of a hand rub.

5. A formulation according to claim 2 in the form of a hand-gel.

6. A method of disinfecting a human or animal body part comprising applying to the body part a formulation according to claim 2.

7. A method according to claim 6 wherein the formulation provides a Log reduction of a bacteriocide activity at least 4.0, about 10-15 seconds after application.

8. A method according to claim 6 wherein the method removes dead skin cells, grease or grime and/or treats minor wounds and/or skin disorders.

9. A method according to claim 6 wherein the formulation is used as an antimicrobial for the pre-operative treatment of skin.

10. A method according to claim 6 wherein the formulation is applied in a pre-operative surgical setting.

11. A method according to claim 6 wherein the formulation is applied to treat insect bites, stings, sun burn or minor skin burns.

12. A method according to claim 6 wherein the formulation is applied to treat or prevent tinea or athlete's foot.

13. A method according to claim 6 wherein the formulation is applied to treat or prevent eczema.

14. A method according to claim 6 wherein the formulation is used as an antimicrobial for the pre-operative treatment of human skin.

* * * * *